United States Patent [19]

Sylvester et al.

[11] 4,102,203
[45] Jul. 25, 1978

[54] UNDERWATER INSPECTION AND COMMUNICATION APPARATUS

[75] Inventors: Bruce J. Sylvester, Duxbury; Roger P. Sylvester, Kingston, both of Mass.

[73] Assignee: J. G. Sylvester Associates, Inc., Rockland, Mass.

[21] Appl. No.: 751,143

[22] Filed: Dec. 16, 1976

[51] Int. Cl.² ............................................ G01N 29/04
[52] U.S. Cl. ..................................... 73/620; 340/3 R
[58] Field of Search ............. 73/67.5 R, 67.7, 67.8 R, 73/170 A, 620, 607; 340/3 R, 5 R, 5 MP; 61/69 R, 69 A

[56] References Cited
U.S. PATENT DOCUMENTS

| | | | |
|---|---|---|---|
| 2,991,445 | 7/1961 | Haynes et al. | 340/3 R |
| 3,045,206 | 7/1962 | Ahrens et al. | 340/3 R |
| 3,119,092 | 1/1964 | Edgerton | 73/170 A |
| 3,354,658 | 11/1967 | Leonardi | 61/69 R |
| 3,426,585 | 2/1969 | Zemanek et al. | 73/67.7 |

*Primary Examiner*—Stephen A. Kreitman
*Attorney, Agent, or Firm*—David G. Conlin

[57] ABSTRACT

A system for non-destructive underwater evaluation of structures comprises an ultrasonic testing means, such as a transducer, means for converting the output thereof into a visual signal, such as an oscilloscope, and means for conveying that visual signal to the underwater technician who is operating the ultrasonic testing means. The means for transmitting the visual signal may comprise an underwater television or other monitor, connected either to a television camera which photographs the output of the oscilloscope or other visual display device, or other means, such as an auxiliary cathode ray tube display device, can be hooked directly to the visual display device. Preferably recording means, such as a video tape recorder, is connected, together with the underwater monitor, to make a permanent record of the monitored signals. Most preferably, the underwater monitor is also attached or attachable to an underwater television camera, so that the inspection can be switched from visual to ultrasonic, or vice versa, at will. Preferably the system also permits direct visual communication between the underwater technician and the topside crew.

10 Claims, 6 Drawing Figures

UNDERWATER INSPECTION AND COMMUNICATION APPARATUS

BACKGROUND OF THE DISCLOSURE

This invention relates to underwater inspection devices, more particularly to underwater ultrasonic inspection devices for detecting fractures, inclusions, faults in welding and the like in underwater steel or other structures.

Preventive maintenance is a concept long established in land based industry. This has proven to be economically the best approach in sustaining the operation of facilities and equipment, as opposed to waiting until failure of such equipment, and then repairing broken structures and machinery. The implementation of preventive maintenance has required development of various means of establishing the operational condition of equipment and structures, and so has evolved various methods of non-destructive inspection and testing. Most structures can now be monitored throughout their service life by non-destructive tests which are extremely effective in detecting the initial breakdown of structures while such breakdowns are still easily correctable, and long before total failure of the structure. In steel structures, radiography, ultrasonics and magnetic particle inspection have developed as the primary means of inspection and testing. There is a similar need for non-destructive inspection and testing of submerged or partly submerged structures, such as the hulls of ships which cannot be dry docked, pilings, pipe lines, supports for off-shore drilling rigs, etc., which are subject to the corrosive and often violent environment of the ocean or other bodies of water.

Because of the criticality of maintaining submerged or partly submerged structures in functional condition, some development has been made in structural inspection and testing for such structures. This development has primarily evolved along the concept of utilization of the same testing and inspection means developed for land based use, and duplication of the land base habitat for which such devices are designed. This is accomplished either by removing the structure from the body of water and examination of the removed structure in a dry environment, or by constructing a dry habitat around the structure while submerged or partly submerged, transporting the testing equipment to the habitat, and performing the inspection or test as it has been performed on dry land. Both of these methods have substantial disadvantages. Both are costly and time consuming. Accordingly, some efforts have been expended in developing specialized test equipment which is portable and manageable in the underwater environment, and permits testing to proceed by straightforward manipulation of these devices by divers. However, such attempts have not met with substantial success, due largely to both the limitations of the underwater environment and the limitations on the abilities of divers to perform complex functions within that environment.

Ultrasonic inspection is a non-destructive testing and inspection method which beams a high frequency sound wave into the material being inspected, the reflections of such sound waves being used to detect surface flaws, subsurface flaws, thickness variations and other types of defects. In the straight beam technique, an ultrasonic probe is placed on one surface of the structure, which probe directs a beam of high frequency sound waves through the structure and listens for reflections of those waves. The sound waves travel through the material with some loss of energy, and are reflected at interfaces. The degree of reflection depends largely on the physical state of the material on the opposite side of the interface, and to a lesser extent on the specific physical properties of the two materials making up the interface. For example, sound waves are almost completely reflected at interfaces between metal and gas, but are only partially reflected at metal-liquid or metal-solid interfaces, and the degree of reflection depends somewhat on the properties of the materials on the opposing sides of the interface.

Ultrasonic inspection techniques provide ready detection of structural faults or discontinuities, including surface or internal cracks, laminations, pores, flaking, bonding faults, shrinkage cavities, and others. See, e.g., "Ultrasonic Inspection", in 11 *Metals Handbook*, pages 161 et seq. (8th ed. 1976). Inclusions of slag or other materials within the structure, even though such inclusions do not act as gas/metal interfaces, can also easily be detected by a variety of techniques, such as causing partial reflection or scattering of the ultrasonic waves, shear wave techniques, and other techniques known in the art.

Ultrasonic inspection devices function by transmitting ultrasonic mechanical vibrations, which impose stresses well below the elastic limit, through the structure being tested, and monitoring the time of transit of the transmitted wave, and reflections of such wave from inclusions, cracks, or the opposing surface of the structure. Many such devices also monitor attenuation or reduction in strength of the beam of sound waves being transmitted. Ultrasonic testing equipment commonly comprises an electronic signal generator that produces bursts of alternating voltage, a sending transducer or probe, which emits a beam of ultrasonic waves in response to the bursts of alternating voltage received from the signal generator, a couplant, which transfers the ultrasonic wave energy from the sending transducer to the test piece, a receiving transducer, to accept the output of ultrasonic waves which have traversed some portion of the test piece and convert such portion of the waves to corresponding bursts of alternating voltage, and devices for amplifying, viewing, and/or recording the signals received from the receiving transducer or probe. Quite often only one transducer is used for both sending and receiving, and that same transducer alternately transmits bursts of such ultrasonic waves and then listens for the response or reflection of those waves. In a typical case, the output of the probe will be amplified, etc., and reproduced visually, e.g. on an oscilloscope, wherein the response is plotted versus time. The thickness of the article being inspected can be gauged by the time transpiring between the transmittal of the ultrasonic signal and its reflections from the opposing surface or wall of the structure. Faults or non-uniformities within the structure appear as tips located between the peak on the visual display device which corresponds to the initial pulse of ultrasonic waves, and the peak which represents the reflection of those waves from the opposed surface of the structure.

As pointed out in the above-noted "Ultrasonic Inspection" article, this method of inspection has many advantages, including superior penetrating power, high sensitivity, and essentially instantaneous evaluation of the results. Also, ultrasonic testing requires availability of only one surface of the structure being tested, and is not hazardous, as compared, e.g., with radiation testing, to the personnel operating or surrounding the testing apparatus. However, as also pointed out in the above-mentioned "Ultrasonic Inspection" article, ultrasonic inspection suffers from the disadvantages that it requires careful attention to the instrument display by experienced technicians in order to obtain proper results, and extensive technical knowledge is necessary in order to interpret the results. Complex manipulation of the probe relative to the instrument display by such trained technicians is necessary in order to optimize readings, determine the size and shape of deformities or inclusions, and differentiate between the various types of faults which can occur, e.g. to differentiate between faults which will not worsen, such as lack of penetration of welds, and faults such as cracks, which may propagate and eventually cause failure of the structure.

The drawbacks inherent in the ultrasonic testing systems have largely curtailed their use in underwater experiments. Operation of such devices in a manner which permits successful detection of anything more than the most basic data, e.g. thickness, requires high skill both in the manipulation of the probe and in the adjustment of the highly complex instruments which display the output of the probe. The standard method for previous attempts at the use of such devices had been for the ultrasonic testing machine to stay on the surface, with a long cable attached to a transducer which a diver brings to the underwater surface to be checked for thickness. Communication between the diver and the technician operating the machine above is achieved through a headset in the diver's helmet. However, the technician operating the machine does not have the ability to move the transducer finite amounts to optimize the readings or determine the size or extent of faults. Nor does the technician/diver have the ability to guide his movements of the probe in conformity with the indications obtained on the ultrasonic testing machine.

As a result of these and other difficulties, no such instruments are available which permit underwater utilization of the ultrasonic technique for those functions in which it is most advantageous, e.g. fault, discontinuity, or inclusion inspection. Although some crude submersible ultrasonic instruments have been developed, they do not have the defect detection of standard ultrasonic testing devices, and are solely utilizable for gauging thickness. Further, all attempts to utilize the ultrasonic machine above the water level or topside, with the diver/technician manipulating the probe in response to orders from a topside technician have been unreliable and inconclusive, due to the inability of the topside technician to communicate the required "feel" to the diver below, to move the transducer various amounts in various directions to optimize readings and determine the size and nature of defects.

It is accordingly an object of the present invention to provide a system which permits utilization of ultrasonic testing for non-destructive underwater inspection and testing of structures, which gives reproducible and reliable analyses for a wide variety of structural defects, and which permits different techniques such as scattering and shear wave techniques, to be used in evaluating the underwater structure. It is a further object of the present invention to provide a system which permits the diver/technician operating an ultrasonic probe to obtain instantaneously the effect of movements of the probe on the article being tested. It is a further object of the present invention to provide a system for ultrasonic underwater testing which provides for immediate and reproducible permanent recordation of the ultrasonic readings obtained, to permit further evaluation after the physical inspection is completed.

These and other objects are obtained in accordance with the present invention, described with reference to the accompanying drawing, in which FIG. 1 is a schematic representation of the components utilized in accordance with one embodiment of the present invention;

In accordance with the present invention, a system is provided under which the diver/technician obtains immediate and positive feedback of the results of his manipulation of the ultrasonic transducer on the structure being analyzed, while at the same time, the primary observation of those results are made, and preferably recorded, by a technician above the surface, who also makes the adjustments necessary to optimize the performance of the ultrasonic testing device, as compared to the placement of the probe, which is done by the diver/technician, without the need for guidance from topside. This direct and positive feedback can be transmitted to the diver in a number of ways. In one embodiment, the output signals of the ultrasonic testing device topside are picked up by a camera in a closed circuit television network and fed to a monitor held in the hand of the diver/technician. In another embodiment, the signals representing the results of the ultrasonic tests or inspection which are fed to the cathode ray tube (CRT) in the ultrasonic testing apparatus, are also fed to a remote CRT maintained in the possession of the diver/technician. In yet another embodiment, the signals obtained from the probe or transducer are directly converted into television image signals by analog circuitry and such signals are transmitted to a closed circuit television monitor in the hands of the diver/technician. Given the present disclosure, suitable analog circuitry for conversion of such signals into television image signals will be readily apparent to the skilled in the art, as will be other possible embodiments of the present invention.

Preferably the results of the manipulation of the probe are transmitted to the diver/technician in the form of television image signals, and reviewed by him on a television monitor, and more preferably, such signals are video recorded simultaneously with transmission to the diver/technician's closed circuit television monitor.

Figure 1:
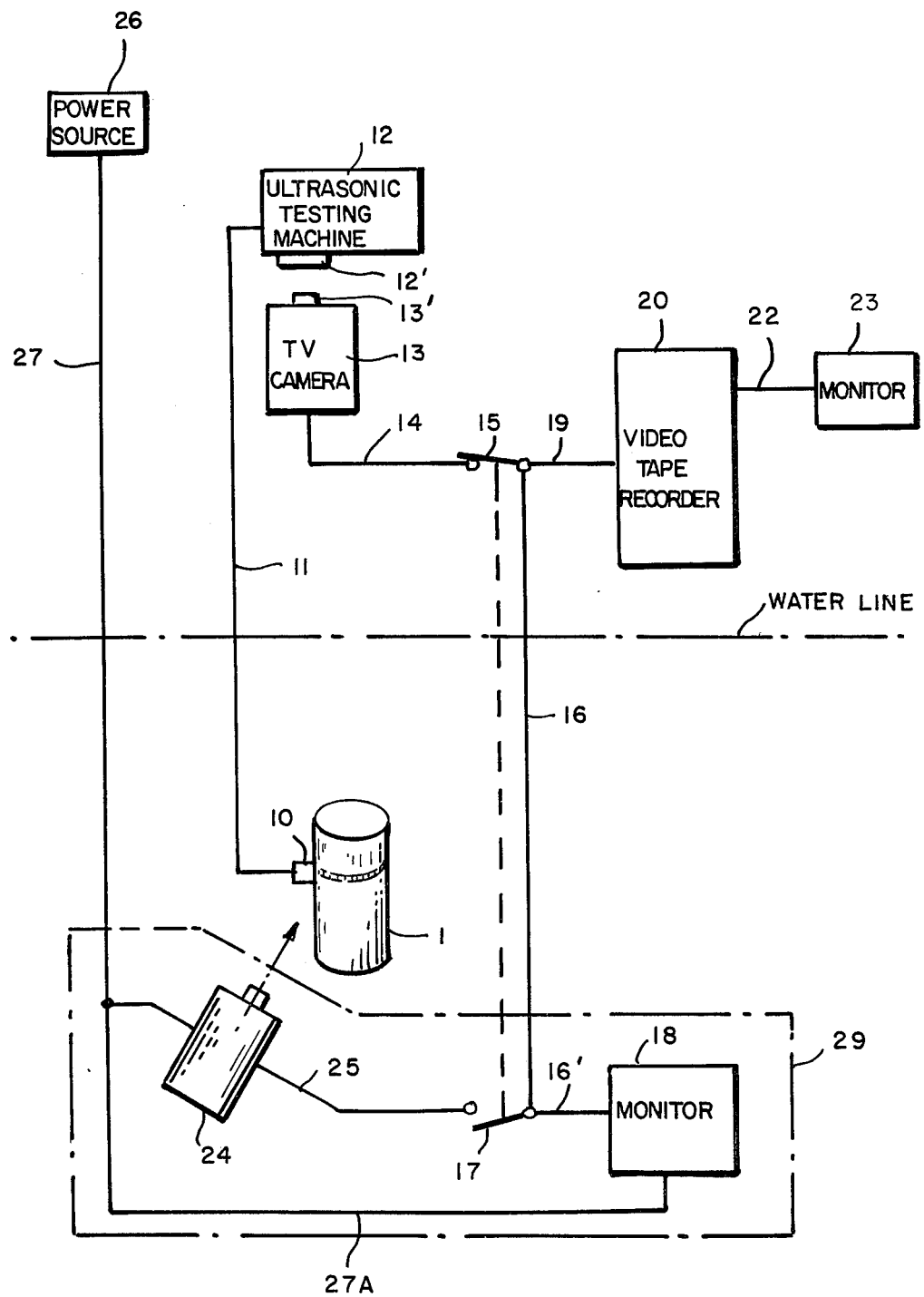

The embodiment of the system most preferred at the present time is depicted schematically in FIG. 1. As there depicted, an ultrasonic probe or transducer 10 is held against an underwater structure 1 to be inspected, with the structure shown having a weld line 1' at a joint. Said structures may typically be supports for bridges, piers, oil platforms, ship hulls, etc. The probe 10 is connected to the ultrasonic testing machine 12 by means of an electrical connection 11, normally a coaxial cable or the like. The probe 10 can be a single element transducer or a double element transducer, both of which are well known in the art. In the single element transducer, the transducer serves both the function of acting as a source of ultrasonic vibrations and acting as a listening or receiving station for ultrasonic reflections. In a dual element transducer, one of the elements operates as the initiator of the ultrasonic vibrations and the other element picks up the reflection or reflective vibrations and signals them to the ultrasonic testing machine.

The ultrasonic testing machine may be a standard model machine, a number of which are commercially available. For example, it may be a sonic model FTS Mark I Ultrasonic Flaw/Thickness Scope, sold by Sonic Instruments, Inc. of Trenton, N.J. Such a machine takes the signals from the transducer or probe, converts them into image signals and displays an image on a repeating oscilloscope screen identified at 12' in FIG. 1. In the embodiment depicted in FIG. 1, closed circuit television camera 13 having lens 13' trained on the oscilloscope image in screen 12' photographs that image, and transmits the image signal through line 14, switch 15, line 16, switch 17 and line 16' to underwater monitor 18, which is kept in the possession of the diver/technician who manipulated probe 10. Preferably, the television image signals are also transmitted through a line 19 into a videotape recording device indicated at 20 in FIG. 1. A television monitor 23 on the surface allows the topside technician to monitor the quality of the image being sent to the diver and being recorded and also allows his comments and interpretation of the inspection to be audio recorded and communicated to the diver. In this particularly desirable embodiment, the results of the ultrasonic testing are recorded, enabling further analysis and reproduction in an easily visible form at some later time, as compared with present systems, in which the only analysis possible is that made by the technician viewing the oscilloscope output. As compared with systems utilizing nonrecorded ultrasonic testing or evaluation, this system is highly beneficial because it permits review and further analysis by others than those actually preformed in taking the measurements. The system also optionally includes monitor 23, through which the topside technician can monitor the working of the closed circuit television and video tape recording system, through signals fed to the monitor via line 22.

In the most preferred system, the diver/technician has in his possession not only the underwater monitor 18, but also a further closed circuit television camera, indicated at 24 in FIG. 1. Under this sytem, the diver/technician can alternately monitor the output of the ultrasonic testing device or observe, transmit and record visual inspection of the structure being inspected and/or the placement of the probe 10, via closed circuit television camera 24. This alternative is engaged when switch 15 is opened, cutting off the television image signals from camera 13 and line 14, and switch 17 is closed, permitting transmission of the television image signals from camera 24 through line 25, switch 17 and line 16' to the monitor 18, so that the diver/technician can see precisely what visual observations are being taken by camera 24. Preferably, such signals are also sent up line 16, through line 19 into videotape recording system 20 and preferably also through line 22 to topside monitor 23. This preferred system is extremely versatile and highly advantageous, and permits for the first time both ultrasonic testing of underwater structures, and visual observation of the precise points being tested ultrasonically. Furthermore, in the preferred embodiment in which the videotape record 20 is employed, there is provided for the first time the ability to record for evaluation both ultrasonic and visual inspection data on submerged structures. Topside visual inspection is also simultaneously provided by use of the monitor 23.

The closed circuit television camera used for underwater work, indicated at 24, should be a high sensitivity, high resolution camera, so that detailed pictures are transmitted under low and poor lighting conditions. Preferably, the camera should be capable of producing clear pictures in dimly lighted areas, having acceptable lighting levels as low as 2 to 5 foot candles or even less. Horizontal and vertical resolutions should be above about 250 lines, preferably at least about 300 lines, or higher. Horizontal resolution is normally higher than vertical resolution, and should be at least 450 lines, preferably 525–550 horizontal lines. Suitable cameras are commercially available, and include Panasonic CC TV camera model WV-241T.

It will be noted that connecting cable 16 serves a dual purpose in the preferred embodiment of this invention. When switch 15 is in a closed position, and switch 17 in the open position, cable 16 carries the television video signals from camera 13 through line 14, down line 16, through line 16' to the underwater monitor 18. When it is desired to utilize the underwater television camera for visual inspection of the work sight, switch 15 is opened and switch 17 is closed, in which case line 16 is utilized to carry the video signals form underwater television camera 24 through line 25, switch 17, line 16, line 19, to video recording instrument 20. Switches 15 and 17 may simply be manually operated by the diver/technician and the topside technician to obtain the desired mode of operation, or, if preferred, switches 15 and 17 can be electromechanically ganged by various devices well known to those skilled in the art, so that the closing of one switch automatically opens the other.

The underwater camera is supplied with electrical power from power source 26, through cable 27. The underwater monitor draws its power from the same source, by a line indicated at 27a in FIG. 1. The power source can be standard 115 volt AC, or it can be converted from 12 volt DC to 115 volt AC by suitable well-known electrical inverters.

Preferably the underwater camera, the monitor, and switch 17 are all mounted together in a single watertight enclosure indicated generally by dotted line 29 in FIG. 1. One embodiment of particularly suitable means for doing this is shown in FIGS. 2 through 6.

Figure 2:
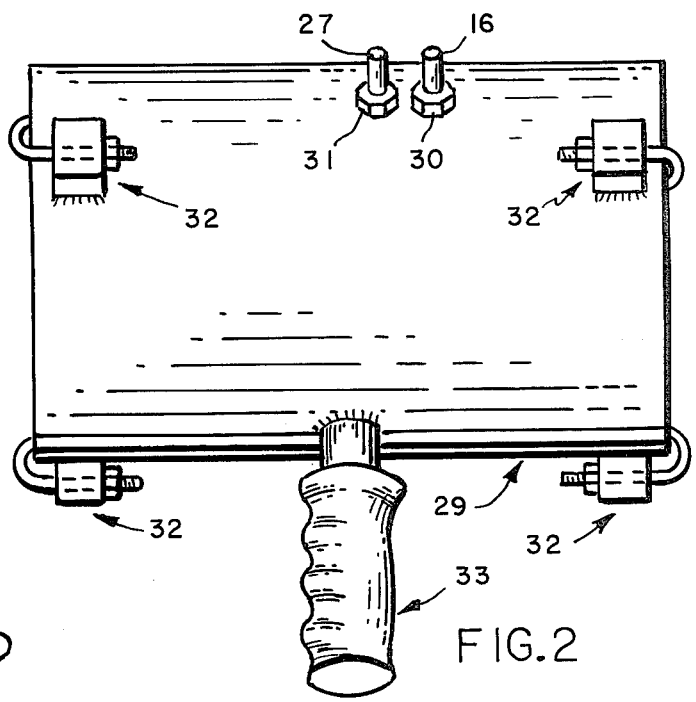
FIG. 2 is a side view of one embodiment of an underwater ultrasonic and visual monitoring and inspection device for use in a system such as that depicted schematically in FIG. 1.

As shown in FIG. 2, the underwater ultrasonic/visual inspection unit comprises a casing 29 bearing suitable watertight connections 30 and 31 for signal cable 16 and power cable 27, respectively. The casing also bears clamps 32, used for holding the end closures of the casing in a watertight seal, and conveniently also bears a hand grip 33 for ease in manipulation by the diver/technician. Preferably the buoyancy of the complete underwater ultrasonic/visual inspection unit is adjusted by addition of suitable ballast, so that the unit either remains vertically motionless or very slowly sinks in the aqueous environment in which it will be used.

Figure 3:
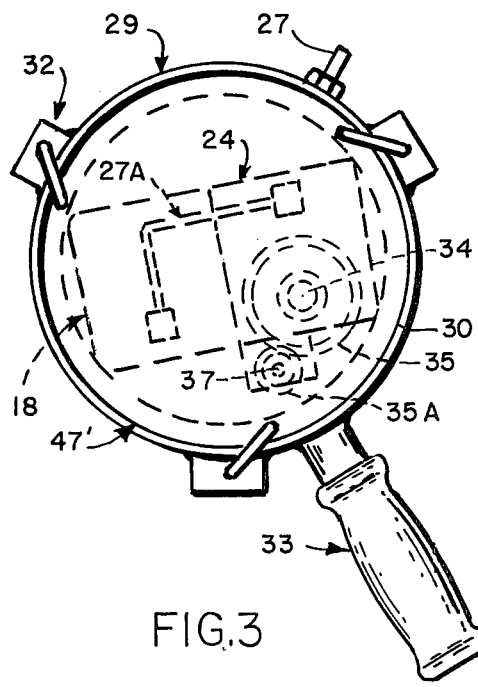
FIG. 3 is an end view of the device depicted in FIG. 2, taken from the left hand side of FIG. 2.
Figure 6:
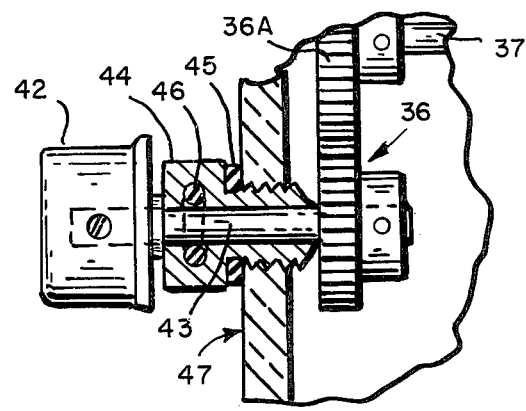
FIG. 6 is a section through a focus control device, taken along section line 6—6 of FIG. 4.

FIG. 3 is an end view of the underwater ultrasonic/visual inspection unit depicted in FIG. 2, as viewed from the left hand side of FIG. 2. Face place 47' closes this end of the unit, and is held in place by clamps 32. In FIG. 3, the underwater camera 24 and the underwater monitor 18 are shown as viewed from the lens end of the camera and from the back end of the monitor. Camera 24 has mounted thereon television lens 34, which is to be aimed at the work sight for visual inspection. Fixedly attached to lens 34 is a toothed gear 35 which matches with gear 35a. Gear 35a is mounted on a rotatable shaft 37. The end of which is shown in FIG. 2, and another portion of which is shown in FIG. 6. Gears 35 and 35a and shaft 37 are utilized by the underwater diver/technician to adjust the focus of the underwater camera, in a manner described herein below. A further embodiment would allow focusing to be performed from the surface via electrical servo motors.

Underwater camera 24 is attached to the power supply line 27 by a suitable connection (not shown) and such power is transferred to the underwater monitor through line 27a.

Figure 4:
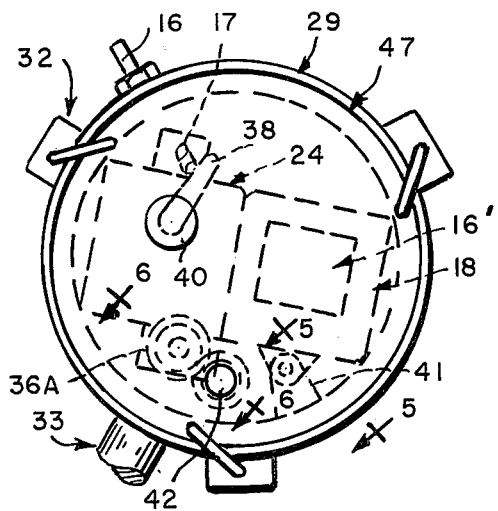
FIG. 4 is an end view of the device of FIG. 2, as seen from the right hand side of FIG. 2.

FIG. 4 shows the underwater ultrasonic/visual inspection unit of FIG. 2 from the right hand side. Shown here is the working end of the monitor 18 and the back end of the underwater camera 24, the monitor 18 having a screen 18'. As further understood with reference to FIG. 6, gear 36a is mounted on this end of axle 37, and meshes with a further gear 36. Gear 36 is fixedly mounted on a further axle 43, which is rotated by knob 42. Axle 43 extends through the end plate 47 and is rotatably borne therein by a watertight fitting 44. Many suitable watertight fittings are well known in the art, the seal against water being maintained in the particular device shown by washer 45 and O-ring 46 in a manner which will be readily apparent to those skilled in the art.

Since this end of the unit is the end which normally faces the diver/technician, in the operating mode where the underwater closed circuit camera is being utilized for visual inspection, the diver/technician views the image obtained on his monitor 18, and can adjust the focus of the camera by turning knob 42, which rotates gears 36, 36a, shaft 37, gears 35a and 35, and thus the standard focusing ring on the camera lens.

Switch 17, which is used for changing from the ultrasonic to the visual mode of inspection, is depicted in FIG. 4 as simple toggle switch, mounted on the top of underwater camera 24. The suitable connection to signal transmission line 16 and to the underwater monitor 18 are not shown in FIG. 4, but will be readily apparently to anybody of ordinary skill in this art. Toggle switch 17 is operated by the diver/technician by means of rotating a knob 40, which is connected by a shaft 60 extending through end piece 47 and is sealed against water pressure, e.g. in a manner similar to the sealing of shaft 43 in FIG. 6. At the other end of shaft 60 is mounted a cam member 38, which can engage toggle switch 17. End pieces 47 and 47' should be made of material which is capable of withstanding the water pressure in the aqueous environment in which the device will be used, and must be transparent at least in those areas overlying the camera lens in end piece 47' and overlying the monitor screen 18' in end piece 47.

Figure 5:
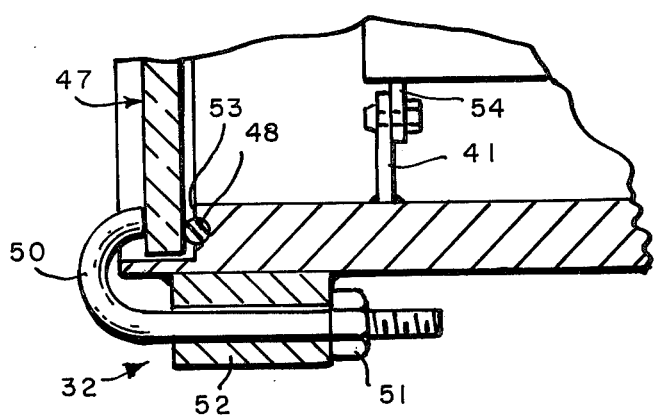
FIG. 5 is a view in section of the closure means and support means in FIG. 4, taken along section line 5—5 of FIG. 4.

Many methods and means for obtaining a watertight seal with end pieces 47 and 47' will be apparent to those skilled in the art. One such means is shown in greater detail in FIG. 5. As there depicted, a J-shaped clamp 50 is threaded on one end, and applies pressure to face plate 47 upon rotation of nut 51, which draws the clamp into the channel in support 52. This prssure causes the end plate 47 to seal snugly against O-ring 48, which is supported by a shoulder 53 formed in the casing 29. After submergence of the unit, the water pressure assits the clamps 32 in maintaining the watertight seal. Also shown in FIG. 5 is a suitable means for supporting the monitor and/or camera within the casing 29. As shown, the means comprises simply a support 41 welded or otherwise attached to the inside of the casing and bolted or otherwise attached to a support 54 which is attached to the monitor and/or camera.

The present underwater inspection system provides for previously unheard of accuracy, reliability, and versitility in underwater testing systems. Whereas previous systems were essentially limited to ultrasonic testing for thickness variations only, the present system provides the capability of making both ultrasonic straight beam and shear wave inspection of submerged structures, materials, and welds, which are probably the most sensitive and effective method of non-destructively testing steel structures. The system described is capable of operation in up to depths of 600 feet or more and allows positive identification of a wide variety of defects, including cracks within the wall of the structure, cracks on the interior surface, or other surface cracks even when concealed by the peening over of the metal adjacent the crack (the so-called "peening effect") or concealed by paint or marine life; slag inclusions within the weld metal; porosity within the weld metal; heat affected zone cracking; lack of penetration of a weld; undercutting at the root of a weld; internal corrosion of the structure; concavity or convexity of a weld; lack of fusion between the weld and the base material; material laminations; stress corrosion cracking; and other defects.

In addition, the preferred system permits a substantial advance in the ability to communicate with the diver/technician concerning the testing procedures. For example, where a television camera is used to communicate the output of the ultrasonic testing device to the diver/technician, the same camera can also be trained on blueprints, for example, of the structure being tested, so that the topside technician can direct the progress of the inspection, and so that the diver/technician can pinpoint the exact portions of the structure which are being tested and/or visually displayed.

While particular embodiments of the present invention have been shown and described, it will be obvious to those skilled in the art that changes and modifications may be made without departing from this invention in its broader aspects. Numerous other specific and unique advantages and applications of the present system will be readily apparent to those of skill in this art, and are intended to come within the scope and spirit of the following claims:

We claim:

1. A system for conducting ultrasonic inspection of a structure submerged below a water surface, comprising;
    a mobile subsurface unit comprising transducer means for transmitting bursts of high frequency sound waves through one surface of said structure and detecting reflections of said sound waves, and monitoring means for monitoring the magnitude of the sonic signals generated by manipulation of the transducer means over the surface of the structure, said transducer means being movable over the surface of said structure apart from the monitoring means; and
    above-surface equipment comprising image-forming means for forming a visual image demonstrating the signals transmitted and detected by said transducer means; connecting means, connected to said image-forming means and said transducer means, for conveying signals transmitted or detected by said transducer means to said image-forming means; and image-transmitting means for transmitting the visual signal formed by the image-forming means to the monitoring means in said subsurface unit.

2. The system of claim 1 further comprising recording means for recording the signals transmitted and detected by said transducer means.

3. The system of claim 1, wherein said image transmitting means comprises a closed circuit television camera and an underwater monitor located proximate said transmitting and detecting means.

4. The system of claim 3, further comprising a video recording means connected to the output of said closed circuit television camera, for recording said images.

5. The system of claim 4, further comprising an underwater television camera located proximate said underwater monitor, for televising visual images of said submerged structure, a first switching means for electrically connecting the output of closed circuit television camera to said underwater monitor and to said video recording means, and a second switching means for electrically connecting the output of said underwater television camera to said underwater monitor and to said video recording means.

6. The system of claim 5, wherein said underwater television camera, said second switching means and said underwater monitor are mounted in a watertight chamber, said chamber comprising means for transmitting electrical power to said underwater television camera and to said underwater monitor, and means for electrically connecting said underwater monitor to said first and second switching means.

7. The system of claim 6, wherein the means for connecting said underwater monitor to said first and second switching means is adapted to transmit the output of said closed circuit television camera to said underwater monitor when each of said first and second switching means is in a first position, and to transmit the output of said underwater television camera to said video recording means when each of said first and second switching means is in a second position.

8. A method of ultrasonically testing a structure submerged beneath a water level, comprising placing an ultrasonic probe on a surface of said structure, converting the output of said ultrasonic probe into a visual image in an above surface ultrasonic testing apparatus, and duplicating said visual image at a location proximate the location of said ultrasonic probe, whereby the manipulator of said ultrasonic probe may observe the output of said probe as the probe is manipulated.

9. The method of claim 8, wherein the visual image is duplicated by televising said image and reproducing said image on an underwater monitor.

10. The method of claim 9, further comprising video recording the visual image as said probe is manipulated.

* * * * *